US012377186B2

(12) United States Patent
Kim et al.

(10) Patent No.: US 12,377,186 B2
(45) Date of Patent: *Aug. 5, 2025

(54) ANTIMICROBIAL BIOPOLYMER COMPOSITIONS, METHODS OF SYNTHESIS, AND APPLICATIONS OF USE

(71) Applicant: ARIZONA BOARD OF REGENTS ON BEHALF OF THE UNIVERSITY OF ARIZONA, Tucson, AZ (US)

(72) Inventors: Minkyu Kim, Tucson, AZ (US); Christopher P. Camp, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 944 days.

This patent is subject to a terminal disclaimer.

(21) Appl. No.: 17/510,220

(22) Filed: Oct. 25, 2021

(65) Prior Publication Data

US 2022/0047770 A1 Feb. 17, 2022

Related U.S. Application Data

(63) Continuation-in-part of application No. 16/253,825, filed on Jan. 22, 2019, now Pat. No. 11,154,636.

(60) Provisional application No. 62/619,430, filed on Jan. 19, 2018.

(51) Int. Cl.
| | |
|---|---|
| *A61L 15/32* | (2006.01) |
| *A61K 38/17* | (2006.01) |
| *A61L 27/22* | (2006.01) |
| *B82Y 5/00* | (2011.01) |
| *B82Y 30/00* | (2011.01) |
| *B82Y 40/00* | (2011.01) |

(52) U.S. Cl.
CPC .......... *A61L 15/32* (2013.01); *A61K 38/1729* (2013.01); *A61L 27/227* (2013.01); *A61L 2300/252* (2013.01); *A61L 2300/404* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS 11,154,636 B2 * 10/2021 Kim ........................ A61L 15/46

OTHER PUBLICATIONS

Despanie et al. "Elastin-Like Polypeptides: Therapeutic Applications for an Emerging Class of Nanomedicines" J. Control Release 240:93-108. (Year: 2016).*
Mahlapuu et al. "Antimicrobial Peptides: An Emerging Category of Therapeutic Agents" Front Cell Infect Microbiol 6:194. (Year: 2016).*
Sousa et al. "Production of a polar fish antimicrobial peptide in *Escherichia coli* using an ELP-intein tag" Journal of Biotechnology 234:83-89. (Year: 2016)*

* cited by examiner

*Primary Examiner* — Melissa L Fisher
*Assistant Examiner* — Zachary J Miknis
(74) *Attorney, Agent, or Firm* — NGUYEN TARBET IP LAW

(57) ABSTRACT

Biopolymer compositions comprising antimicrobial peptides (AMPs) for treating infections such as bacterial infections, viral infections, fungal infections, and parasitic infections. The compositions herein may also be used for treating infections associated with antibiotic-resistant bacteria, antifungal-resistant fungi, antiviral-resistant viruses, or for treating biological warfare agents (BWAs) such as *Bacillus anthracis* and *Yersenia pestis*. The present invention also provides methods of synthesis of said biopolymer compositions, wherein AMP biopolymers can be synthesized as an artificially engineered protein by genetically fusing an AMP; a protein that behaves similarly to polymer tethers; and a protein as a modifiable material platform that can transform to self-assembled nanoparticles, self-standing films, or adhesives to easily attach tethered AMPs onto any biomaterial surface for various clinical applications.

19 Claims, 2 Drawing Sheets
Specification includes a Sequence Listing.

Nanoparticle Drugs

Wound Dressings

Underwater Coatings 24X, 36x in PBS ~1.2 mg/mL, Heating rate 1 C/min

SEQUENCE LISTING

```
<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)
<220> FEATURE:
<221> NAME/KEY: MISC_FEATURE
<222> LOCATION: (4)..(4)
<223> OTHER INFORMATION: any naturally occurring amino acid except Pro.

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)
<220> FEATURE:
<221> NAME/KEY: MISC_FEATURE
<222> LOCATION: (1)..(1)
<223> OTHER INFORMATION: Val, Ile, Leu
<220> FEATURE:
<221> NAME/KEY: MISC_FEATURE
<222> LOCATION: (3)..(3)
<223> OTHER INFORMATION: any naturally occuring amino acid
<220> FEATURE:
<221> NAME/KEY: MISC_FEATURE
<222> LOCATION: (4)..(4)
<223> OTHER INFORMATION: any naturally occuring amino acid except
      proline

<400> SEQUENCE: 2

Xaa Pro Xaa Xaa Gly
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 3

Val Pro Gly Tyr Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 4

Val Pro Gly Ala Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 5

Val Pro Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 6

Val Pro Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 7

Val Pro Gly Arg Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 8
```

Val Pro Gly Asn Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 9

Val Pro Gly Asp Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 10

Val Pro Gly Cys Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 11

Val Pro Gly Gln Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 12

Val Pro Gly Glu Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 13

Val Pro Gly His Gly
1               5

<210> SEQ ID NO 14
<211> LENGTH: 5
<212> TYPE: PRT
<213> ORGANISM: Artificial Sequence

```
<220> FEATURE:
<223> OTHER INFORMATION: Pentapeptide repeat of an elastin-like
      polypeptide (ELP)

<400> SEQUENCE: 14

Val Pro Gly Ile Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 15

Val Pro Gly Leu Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 16

Val Pro Gly Lys Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 17

Val Pro Gly Met Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 18

Val Pro Gly Phe Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 19

Val Pro Gly Thr Gly
1               5
```

```
<210> SEQ ID NO 20
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 20

Val Pro Gly Trp Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 21

Val Pro Gly Val Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 22

Val Gly Gly Val Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 23

Lys Gly Gly Val Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 24

Val Pro Tyr Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)
```

```
<400> SEQUENCE: 25

Val Pro Tyr Val Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 26

Val Pro Tyr Asn Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 27

Val Pro Tyr Cys Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 28

Val Pro Tyr Leu Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 29

Val Pro Asn Gly Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 30

Ile Pro Gly Tyr Gly
1               5

<210> SEQ ID NO 31
<211> LENGTH: 5
<212> TYPE: PRT
```

```
<213> ORGANISM: Artificial Sequence
<220> FEATURE:
<223> OTHER INFORMATION: Pentapeptide repeat of an elastin-like
      polypeptide (ELP)

<400> SEQUENCE: 31

Ile Pro Gly Val Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 32

Ile Pro Tyr Gly Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 33

Ile Pro Tyr Val Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 34

Ile Pro Tyr Leu Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 35

Ile Pro Asn Gly Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 36

Leu Pro Gly Tyr Gly
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 37

Leu Pro Gly Val Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 38

Leu Pro Tyr Gly Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 39

Leu Pro Tyr Val Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 40

Leu Pro Tyr Leu Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Pentapeptide repeat of an elastin-like
      polypeptide (ELP)

<400> SEQUENCE: 41

Leu Pro Asn Gly Gly
1               5

<210> SEQ ID NO 42
<211> LENGTH: 5
<212> TYPE: PRT
<213> ORGANISM: Artificial Sequence
<220> FEATURE:
<223> OTHER INFORMATION: peptide tether
```

```
<400> SEQUENCE: 42

Val Ser Gly Ser Gly
1               5

<210> SEQ ID NO 43
<211> LENGTH: 9
<212> TYPE: PRT
<213> ORGANISM: Artificial Sequence
<220> FEATURE:
<223> OTHER INFORMATION: peptide tether

<400> SEQUENCE: 43

Ala Gly Ala Gly Ala Gly Pro Glu Gly
1               5

<210> SEQ ID NO 44
<211> LENGTH: 5
<212> TYPE: PRT
<213> ORGANISM: Artificial Sequence
<220> FEATURE:
<223> OTHER INFORMATION: peptide tether

<400> SEQUENCE: 44

Val Pro Gly Ala Gly
1               5

<210> SEQ ID NO 45
<211> LENGTH: 5
<212> TYPE: PRT
<213> ORGANISM: Artificial Sequence
<220> FEATURE:
<223> OTHER INFORMATION: peptide tether

<400> SEQUENCE: 45

Val Pro Gly Gly Gly
1               5

<210> SEQ ID NO 46
<211> LENGTH: 5
<212> TYPE: PRT
<213> ORGANISM: Artificial Sequence
<220> FEATURE:
<223> OTHER INFORMATION: peptide tether

<400> SEQUENCE: 46

Val Pro Gly Glu Gly
1               5

<210> SEQ ID NO 47
<211> LENGTH: 10
<212> TYPE: PRT
<213> ORGANISM: Artificial Sequence
<220> FEATURE:
<223> OTHER INFORMATION: peptide tether

<400> SEQUENCE: 47

Val Pro Gly Glu Gly Val Pro Gly Lys Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: peptide tether

<400> SEQUENCE: 48
```

```
Ala Gly Ala Gly Ala Gly Pro Glu Gly
1               5

<210> SEQ ID NO 49
<211> LENGTH: 21
<212> TYPE: PRT
<213> ORGANISM: Artificial Sequence
<220> FEATURE:
<223> OTHER INFORMATION: peptide tether

<400> SEQUENCE: 49

Ala Ser Pro Ala Ala Pro Ala Pro Ala Ser Pro Ala Ala Pro Ala Pro
1               5                   10                  15

Ser Ala Pro Ala Ala
            20

<210> SEQ ID NO 50
<211> LENGTH: 108
<212> TYPE: PRT
<213> ORGANISM: Artificial Sequence
<220> FEATURE:
<223> OTHER INFORMATION: peptide tether

<400> SEQUENCE: 50

Gly Glu Gln Gly Lys Pro Gly Asn Gln Gly Glu Pro Gly Asn Pro Gly
1               5                   10                  15

Ser Pro Gly Gln Pro Gly Asn Pro Gly Gln Pro Gly Ser Pro Gly Asn
            20                  25                  30

Pro Gly Gln Pro Gly Asn Glu Gly Pro Gln Gly Ser Gln Gly Asn Pro
            35                  40                  45

Gly Gln Pro Gly Glu Pro Gly Ser Asn Gly Gln Pro Gly Gln Pro Gly
            50                  55                  60

Gln Asn Gly Lys Asn Gly Gln Pro Gly Ser Pro Gly Ser Gln Gly Ser
65                  70                  75                  80

Pro Gly Asn Gln Gly Ser Pro Gly Asn Gln Gly Gln Pro Gly Asn Lys
            85                  90                  95

Gly Glu Gln Gly Lys Pro Gly Asn Gln Gly Pro Ala
            100                 105

<210> SEQ ID NO 51
<211> LENGTH: 37
<212> TYPE: PRT
<213> ORGANISM: Artificial Sequence
<220> FEATURE:
<223> OTHER INFORMATION: Antimicrobial peptide LL37

<400> SEQUENCE: 51

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

ANTIMICROBIAL BIOPOLYMER COMPOSITIONS, METHODS OF SYNTHESIS, AND APPLICATIONS OF USE

CROSS-REFERENCES TO RELATED APPLICATIONS

This application is a continuation-in-part and claims benefit of U.S. patent application Ser. No. 16/253,825 filed Jan. 22, 2019, which is a non-provisional and claims benefit of U.S. Patent Application No. 62/619,430 filed Jan. 19, 2018, the specifications of which are incorporated herein in its entirety by reference.

REFERENCE TO A SEQUENCE LISTING

Applicant asserts that the paper copy of the Sequence Listing is identical to the Sequence Listing in computer readable form found on the accompanying computer file, entitled UNIA 17.44 CIP Sequence Listing_ST25. The content of the sequence listing is incorporated herein by reference in its entirety.

FIELD OF THE INVENTION

The present invention relates to biopolymers, more particularly to biopolymers comprising tethered antimicrobial peptides (AMPs) for treating microbial infections.

BACKGROUND OF THE INVENTION

Tethering antimicrobial peptides (AMPs) to a biomaterial surface is a promising therapeutic to treat a broad range of microbial infections (e.g., by enhancing AMP stability, prolonging AMP activity in vivo, reducing AMP dosage, reducing AMP toxicity, etc.), including antimicrobial-resistant microorganisms. However, complex chemical synthesis of conventional AMP-incorporated materials limits the use of antimicrobial materials in clinical settings. Furthermore, the complex chemical synthesis and processing of conventional AMP-incorporated materials is impractical for many AMPs due to high cost burdens. For example, conventional AMP-incorporated materials are comprised of: an AMP; a long, flexible, hydrophilic polymer tether; and a biomaterial that is specific to the clinical application. Each component is synthesized individually and subsequently connected in additional steps.

AMP biopolymers can be synthesized as an artificially engineered protein (an "all-in-one" artificial protein) by genetically fusing (1) an AMP; (2) a protein that behaves similarly to polymer tethers; and (3) a protein as a modifiable material platform that can transform to self-standing nanoparticles and films, or adhesives to easily attach tethered AMPs onto any biomaterial surface for various clinical applications. Genetic engineering allows for modification of single amino acids of the artificial protein, e.g., for modifying the AMP sequence for better potency, changing to a different AMP, improving the material properties, etc. Biosynthesis using biological hosts precisely produces the artificial proteins as designed, reducing inconsistent antimicrobial activity by eliminating complex chemical processing. In addition, because these proteins can be purified without traditional chromatography, and because biosynthesis is scalable, there is significant potential for the clinical translation of the AMP-incorporated materials using cost-effective biomanufacturing.

The development of this "all-in-one" artificial protein as a universal material platform for AMPs serves to mitigate current barriers to the efficient and cost-effective development and application of AMP-incorporated materials for their use in the clinical setting.

SUMMARY OF THE INVENTION

The present invention features biopolymers comprising antimicrobial peptides (AMPs), as well as applications of use, methods of synthesis, and compositions for synthesis. The methods and compositions herein help to simplify and unify the synthesis of various AMP-incorporated materials.

The biopolymers of the present invention may be used for treating microbial infections, including bacterial infections, fungal infections, parasitic infections, viral infections, infections associated with antibiotic-resistant bacteria or antifungal-resistant fungi or antiviral-resistant viruses, biological warfare agents (BWAs) such as *Bacillus anthracis* and *Yersenia pestis*, etc. The biopolymers of the present invention may be used to kill or reduce the growth of the particular microbe (e.g., bacteria, fungus, parasite, virus, etc.).

The ELP(Tyr) design provided herein produces AMP antimicrobial agents in the form of nanoparticles, films/membranes, and strong adhesives to biomaterial surfaces. Elastin-like polypeptide (ELP)-fusion proteins self-assemble into multiple material structures in physiological conditions as a function of: (i) the designed phase transition temperature (Tt); (ii) molar mass ratio between the ELP and fused proteins; and (iii) concentration of ELP-fusion protein in solution. This helps guide the development of AMP nanoparticles.

The present invention provides antimicrobial material (AMP)-biopolymer compositions comprising an elastin-like polypeptide (ELP); an antimicrobial material (AMP); and a protein (polypeptide, e.g., with antifouling characteristics) tether connecting the ELP and the AMP. In certain embodiments, the ELP comprises at least one tyrosine residue (e.g., ELP(Tyr)). In certain embodiments, the ELP, e.g., ELP(Tyr), is according to the formula (VPGXaaG)$_m$ (SEQ ID NO: 1). In certain embodiments, the ELP, e.g., ELP(Tyr), is according to the formula [(VPGXaaG)$_j$(VPGYG)$_k$(VPGXaaG)$_l$]$_n$ (note VPGYG is SEQ ID NO: 2), thus the formula may be written [(SEQ ID NO: 1)$_j$(SEQ ID NO: 2)$_k$(SEQ ID NO: 1)$_l$]$_n$. In certain embodiments, Xaa is a polar amino acid, a non-polar amino acid, a charged amino acid, or a combination thereof, not including proline. For example, in certain embodiments, Xaa is alanine. In some embodiments, Xaa is serine. In some embodiments, Xaa is glycine. In some embodiments, Xaa is arginine. In some embodiments, Xaa is asparagine. In some embodiments, Xaa is aspartic acid. In some embodiments, Xaa is cysteine. In some embodiments, Xaa is glutamine. In some embodiments, Xaa is glutamic acid. In some embodiments, Xaa is histidine. In some embodiments, Xaa is isoleucine. In some embodiments, Xaa is leucine. In some embodiments, Xaa is lysine. In some embodiments, Xaa is methionine. In some embodiments, Xaa is phenylalanine. In some embodiments, Xaa is threonine. In some embodiments, Xaa is tryptophan. In some embodiments, Xaa is tyrosine. In some embodiments, Xaa is valine. In some embodiments, Xaa may be one or a combination of the aforementioned examples of amino acids. A composition may comprise a plurality of ELPs with one or different formulas.

Certain embodiments herein, e.g., compositions herein, may comprise an elastin-like peptide (ELP), an antimicrobial peptide (AMP) and a hydrophilic protein tether connecting the ELP and the AMP. In some embodiments, the ELP comprises one or more pentapeptide repeats consecutively linked. In other embodiments, at least one of the pentapeptide repeats comprises a tyrosine residue. In some embodiments, protein tether connects to the AMP at the AMP's N-terminus, C-terminus, or both. In further embodiments, the ELP is more hydrophobic than the protein tether.

The present invention also features antimicrobial material (AMP)-biopolymer compositions comprising: an elastin-like polypeptide (ELP); an antimicrobial material (AMP); and a protein tether connecting the ELP and the AMP, wherein the peptide tether connects to the AMP at the AMP's N-terminus or C-terminus. In some embodiments, the ELP comprises at least one tyrosine residue.

The ELP may be according to the formula [(VPGXaaG, SEQ ID NO: 1)$_j$(VPGYG, SEQ ID NO: 2)$_k$(VPGXaaG, SEQ ID NO: 1)$_l$]$_n$. In some embodiments, Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, or valine.

In some embodiments, the protein tether comprises [VPGSG]$_i$ (SEQ ID NO: 4) or [AGAGAGPEG]$_n$ (SEQ ID NO: 5). In some embodiments, the composition self-assembles into nanoparticles. In some embodiments, tyrosine residues are cross-linked to form a self-standing film, a membrane material, or a hydrogel.

In some embodiments, the tyrosine residue allows the composition to adhere to a surface after hydroxylation by tyrosinase. In other embodiments, the tyrosine residue allows the composition to adhere to a surface after hydroxylation. In some embodiments, the surface is a cloth, a plastic, a glass, a metal, or a combination thereof. In some embodiments, the surface is a medical device, a dressing, a clothing, or a combination thereof. In some embodiments, the protein tether has anti-fouling characteristics. In some embodiments, the composition is for killing an infectious agent or for reducing growth of an infectious agent. In some embodiments, the infectious agent is a bacteria, a virus, a fungus, or a parasite.

In certain embodiments, the AMP is selected from the group consisting of LL37, RL37, Dermcidin, Protegrin (e.g., PG-1, PG-2, PG-3, PG-4, or PG-5), Pexiganan, etc., or a combination thereof. However, the present invention is not limited to the aforementioned AMPs.

In certain embodiments, the AMP biopolymer composition self-assembles into nanoparticles. In certain embodiments, the tyrosine residues are cross-linked (e.g., by photo-crosslinking using a photoinitiator, e.g., riboflavin (vitamin B2), Tris(2,2-bipyridine) ruthenium (II), etc., to form a self-standing film, a membrane material, or a hydrogel.

The tyrosine residue(s) of the composition allow the composition to adhere to a surface (e.g., cloth, plastic, metal, glass, a combination thereof; e.g., a medical device such as an endoscope or an implant, a dressing, clothing, or a combination thereof), e.g., after hydroxylation by tyrosinase.

In certain embodiments, AMP is connected to the tether by its N-terminus. In certain embodiments, the AMP is connected to the tether by its C-terminus. In certain embodiments, the composition comprises an AMP molecule connected to the tether at its N-terminus and an AMP molecule connected to the tether at its C-terminus. For example, in certain embodiments, the composition is ELP(Tyr)-tether-AMP. In certain embodiments, the composition is AMP-tether-ELP(Tyr). In certain embodiments, the composition is ELP-tether-AMP. In certain embodiments, the composition is AMP-tether-ELP. In certain embodiments, the composition comprises a mix of different compositions, e.g., a mix of AMP-tether-ELP and ELP-tether-AMP.

In certain embodiments, the composition is for treating an infection, e.g., a bacterial infection, a viral infection, a fungal infection, or a parasitic infection. In certain embodiments, the infection is caused by a biological warfare agent. In certain embodiments, the infection is caused by an antimicrobial-resistant microorganism. In certain embodiments, the composition is for killing an infectious agent or for reducing growth of an infectious agent.

The present invention also provides films comprising an antimicrobial material (AMP)-biopolymer according to the present invention as described herein. For example, the AMP-biopolymer may comprise an elastin-like polypeptide (ELP) (e.g., ELP(Tyr)); an antimicrobial peptide (AMP); and a protein tether connecting the ELP and the AMP. In some embodiments, the AMP-biopolymer comprises: an elastin-like polypeptide ELP(Tyr) according to the formula [(VPGXaaG, SEQ ID NO: 1)$_j$(VPGYG, SEQ ID NO: 3)$_k$(VPGXaaG, SEQ ID NO: 1)$_l$]$_n$; an antimicrobial peptide (AMP); and a protein tether connecting the ELP and the AMP. The protein tether connects to the AMP at the AMP's N-terminus or C-terminus. The ELP may be cross-linked to form the film material. For example, the tyrosines in the ELP(Tyr) may be cross-linked to form a film.

In some embodiments, Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, or valine. In some embodiments, the AMP is selected from the group consisting of LL37, RL37, Dermcidin, Protegrin, Pexiganan or a combination thereof. However, the present invention is not limited to the aforementioned AMPs. In some embodiments, the protein tether comprises [VPGSG]$_i$ (SEQ ID NO: 42) or [AGAGAGPEG]$_i$ (SEQ ID NO: 43).

The present invention also provides therapeutic cocktail compositions comprising two or more different antimicrobial (AMP)-biopolymer compositions according to the present invention. For example, in some embodiments, each AMP biopolymer composition comprises an elastin-like polypeptide ELP(Tyr) according to the formula [(VPGXaaG, SEQ ID NO: 1)$_j$ (VPGYG, SEQ ID NO: 3)$_k$(VPGXaaG, SEQ ID NO: 1)$_l$]$_n$; an antimicrobial peptide (AMP); and a protein tether connecting the ELP and the AMP. The protein tether may connect to the AMP at the AMP's N-terminus or C-terminus. In some embodiments, the AMP is selected from the group consisting of LL37, RL37, Dermcidin, Protegrin, Pexiganan or a combination thereof. However, the AMP is not limited to the aforementioned examples of AMPs.

The present invention also provides designed nucleic acid sequences encoding AMP-biopolymer compositions according to the present invention. The present invention also features isolated nucleic acid sequences encoding AMP-biopolymer compositions according to the present invention. The present invention also provides amino acid sequences of AMP-biopolymer compositions according to the present invention.

The present invention also provides methods of synthesizing AMP-biopolymer compositions according to the present invention. In certain embodiments, the method comprises introducing (to a host for gene expression such as but not limited to a bacterial host) a vector encoding the AMP-biopolymer composition; expressing the AMP-biopolymer composition; and purifying the AMP-biopolymer composition. In certain embodiments, the gene expression host is a bacterial host, e.g., *Escherichia coli*. The gene expression host is not limited to *E. coli*. In certain embodiments, purifying the AMP biopolymer composition comprises an inverse transition cycling (ITC) method.

The present invention also provides methods for purifying AMP biopolymer compositions according to the present invention, wherein the method comprises an inverse transition cycling (ITC) method.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed descriptions presented in connection with the accompanying drawings in which.

DETAILED DESCRIPTION OF THE INVENTION

Figure 1:
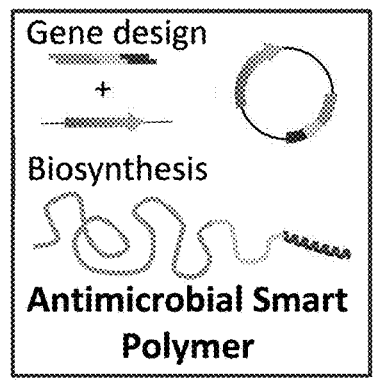
FIG. 1 shows a schematic view of the synthesis of AMP biopolymers (e.g., ELPs) of the present invention as well as applications thereof.
Figure 1:
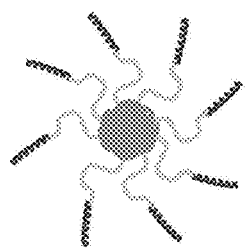
Figure 1:
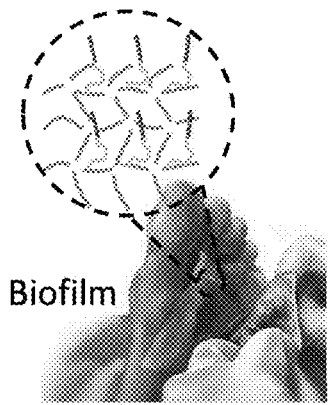
Figure 1:
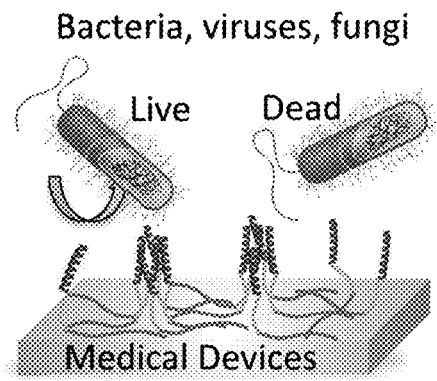

For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

As used herein, the "amino acids" refers to the twenty amino acids that are found in nature, i.e. occur naturally. The natural amino acids are as follows: alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine. This application adheres to the IUPAC rules of standard abbreviations for amino acids.

A conservative substitution, as known to one of ordinary skill in the art, refers to a complete replacement of an amino acid residue with a different residue having similar biochemical characteristics, such as size, charge, polarity, etc. For instance, the aromatic Tyrosine may be conservatively substituted with aromatic phenylalanine, or basic Arginine may be conservatively substituted with basic Lysine. TABLE 1A and 1B show non-limiting examples of conservative amino acid substitutions.

TABLE 1A

| Original Residue | Conservative Substitutions |
|---|---|
| Ala (A) | Cys, Gly, Ser, Thr, Val |
| Arg (R) | Asn, Gln, Glu, His, Lys |
| Asn (N) | Arg, Asp, Gln, Glu, His, Lys, Ser, Thr |
| Asp (D) | Asn, Gln, Glu, Ser |
| Cys (C) | Ala, Ser |
| Gln (Q) | Arg, Asn, Asp, Glu, His, Lys, Met, Ser |
| Glu (E) | Arg, Asn, Asp, Gln, His, Lys, Ser |
| Gly (G) | Ala, Ser, Glu, Asp |
| Ile (I) | Leu, Met, Phe, Val |
| Leu (L) | Ile, Met, Phe, Val |
| Lys (K) | Arg, Asn, Gln, Glu, Ser |
| Met (M) | Gln, Ile, Leu, Phe, Val |
| Phe (F) | Ile, Leu, Met, Trp, Tyr |
| Pro (P) | None |
| Ser (S) | Ala, Asn, Asp, Gln, Glu, Gly, Lys, Thr |
| Thr (T) | Ala, Asn, Ser, Val |
| Trp (W) | Phe, Tyr |
| Tyr (Y) | His, Phe, Trp, |
| Val (V) | Ala, Ile, Leu, Met, Thr |

TABLE 1B

| Amino Acid Property | Amino Add Substitutions |
|---|---|
| Hydrophobic | Cys, Ile, Leu, Met, Phe, Pro, Trp, Val |
| Aliphatic | Ala, Ile, Leu, Pro, Val |
| Aromatic | His, Phe, Trp, Tyr |
| Amide | Asn, Gln |
| Nucleophilic | Cys, Ser, Thr |

TABLE 1B-continued

| Amino Acid Property | Amino Add Substitutions |
| --- | --- |
| Polar | Arg, Asp, Asn, Gln, Glu, Lys |
| Negative | Asp, Glu |
| Positive | Arg, Lys, His |
| Small | Ala, Gly, Pro, Ser |
| C-beta | Ile, Thr, Val |

As used herein, "micelle" and "nanoparticle" may be used interchangeably and refer to self-assembled molecules. In some embodiments, a nanoparticle describes a micelle of a particular size (i.e., nanoscale micelle).

The present invention features biopolymers comprising antimicrobial peptides (AMPs), as well as applications of use, methods of synthesis, and compositions for synthesis. The present invention provides compositions (e.g., a material platform) that stabilize AMPs and helps improve the ability to use AMPs as therapeutic agents for treating infections, e.g., bacterial infections, fungal infections, parasitic infections, viral infections, infections associated with antibiotic-resistant bacteria or antifungal-resistant fungi or antiviral-resistant viruses, biological warfare agents (BWAs) such as *Bacillus anthracis* and *Yersenia pestis*, etc. The biopolymers of the present invention may be used to kill or reduce the growth of the particular microbe or infectious agent (e.g., bacteria, fungus, parasite, virus, etc.).

Certain embodiments herein, e.g., compositions herein, may comprise an elastin-like peptide (ELP), an antimicrobial peptide (AMP) and a hydrophilic protein tether connecting the ELP and the AMP. In some embodiments, the ELP comprises one or more pentapeptide repeats consecutively linked. In other embodiments, at least one of the pentapeptide repeats comprises a tyrosine residue. In some embodiments, protein tether connects to the AMP at the AMP's N-terminus, C-terminus, or both. In further embodiments, the ELP is more hydrophobic than the protein tether. In further embodiments, the composition described herein self-assembles into nanoparticles In some embodiments, the one or more pentapeptide repeat is according to the formula (WaaPXaaYaaG (SEQ ID NO: 2))$_m$, where Waa is valine, isoleucine or leucine, where Xaa is any amino acid, where Yaa is any amino acid except for proline, and where m is 10 to 400. In other embodiments, the one or more pentapeptide repeat is according to the formula (VPGXaaG (SEQ ID NO: 1))$_m$, where Xaa is any amino acid except for proline and where m is from 10 to 400.

In further embodiments, the one or more pentapeptide repeats is selected from a group consisting of: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. In certain embodiments, the one or more pentapeptide repeats comprising the tyrosine is selected from a group consisting of SEQ ID NO: 3, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 33, SEQ ID NO: 34, SEQ ID NO: 36, SEQ ID NO: 38, SEQ ID NO: 39, and SEQ ID NO: 40.

In some embodiments, the tyrosine residues are cross-linked to form a self-standing film, a membrane material, or a hydrogel. In some embodiments, the tyrosine residue allows the composition to adhere to a surface after hydroxylation. In other embodiments, the tyrosine residue allows the composition to adhere to a surface after hydroxylation by tyrosinase. In some embodiments, the surface is a cloth, a plastic, a glass, a metal, or a combination thereof. In other embodiments, the surface is a medical device, a dressing, a clothing, or a combination thereof.

The present invention discloses AMP-biopolymer compositions and methods for synthesizing the AMP-biopolymer compositions by integrating the synthesis of the AMP, the tether, and a biomaterial. To enable this approach, the biomaterial (platform, scaffold) may need to be able to transform into self-assembled nanoparticles, into adhesives to form a coating, and/or cross-link to form a film, gel, filter, antimicrobial clothing material, etc. The biopolymer may also need to contain a region that behaves structurally and physically similar to polymer tethers for enhanced AMP activity and stability.

The AMP biopolymer compositions (e.g., platforms, scaffolds) feature (1) a biocompatible scaffold (e.g., elastin-like polypeptide (ELP), resilin-like polypeptide (RLP), etc.); (2) a protein tether, and (3) an AMP. Without wishing to limit the present invention to any theory or mechanism, it is believed that the ELP platform is advantageous because of its tractability to transform into many types of biomaterials: (i) biocompatible ELP self-assembles into nanoparticles when heated above its phase-transitioning temperature (Tt), (ii) covalently bonded Tyr residues can form a self-standing film or membrane, and (iii) Tyr hydroxylation allows Tyr-containing materials to strongly adhere to surfaces. FIG. 1 illustrates the overall strategy of the compositions (e.g., ELPs) herein, wherein AMP biopolymers can be designed and synthesized as a single unit. A gene is designed to yield a particular ELP (e.g., ELP(Tyr)) linked to a tether linked to an AMP, wherein the whole unit is called the biopolymer. Because the biopolymer is designed at the genetic level, modification of the components can be made by altering the nucleic acid sequence that encodes the biopolymer through genetic engineering. The biopolymer can self-assemble, e.g., to create a nanoparticle drug. In some embodiments, the tyrosine residues are utilized for photo-crosslinking or for attaching to surfaces such as but not limited to medical device surfaces or clothing, or for creating a biofilm for applications such as wound dressings.

Elastin-Like Polypeptide (ELP) Scaffold

As used herein, "elastin-like polypeptides (ELPs)" refer to a class of artificial, disordered polypeptide polymers comprising repeats of short peptide motifs. For example, an ELP may comprise pentapeptide repeat units (e.g., VPGXaaG (SEQ ID NO: 1)—where Xaa can be any amino acid except proline. In some embodiments, ELPs are based on the sequence of an elastin protein, an extracellular matrix protein that provides elasticity to tissues such as arteries, lungs, and skin. In other embodiments, the ELPs are derived from the hydrophobic domain of tropoelastin.

In some embodiments, the scaffold component of the AMP biopolymer compositions described herein may comprise an elastin-like polypeptide (ELP). In some embodiments, the ELP comprises pentapeptide repeats such as (VPGXaaG (SEQ ID NO: 1))$_m$, where Xaa is any amino acid except for proline and where m is from 10 to 400. In some embodiments, when two or more pentapeptide repeats such as (VPGXaaG (SEQ ID NO: 1))$_m$ are consecutively linked together Xaa may be one or a plurality of amino acids (not including proline) (e.g., polar amino acids, non-polar amino acids, charged amino acids, or a combination thereof). For example, an ELP may comprise the sequence ((VPGXaaG (SEQ ID NO: 1))$_m$ (VPGXaaG (SEQ ID NO: 1))$_m$), where both Xaa are the same amino acid (e.g., Y; i.e., ((VPGYG (SEQ ID NO: 3))$_m$ (VPGYG (SEQ ID NO: 3))$_m$), or where the Xaa are two different amino (e.g., Y and A; i.e., ((VPGYG (SEQ ID NO: 3))$_m$ (VPGAG (SEQ ID NO: 4))$_m$). In other embodiments, the ELP comprises a pentapeptide repeats such as (WaaPXaaYaaG (SEQ ID NO: 2))$_m$, where Waa in position 1 is valine, isoleucine or leucine, where Xaa in position 3 is any amino acid, where Yaa in position 4 is any amino acid except for proline, and where m is 10 to 400.

In certain embodiments, m is 10. In other embodiments, m is a number from 10 to 15, or from 10 to 20, or from 10 to 25, or from 10 to 50, or from 10 to 100, or from 10 to 150, or from 10 to 200, or from 10 to 250, or from 10 to 300, or from 10 to 350, or from 10 to 400, or from 10 to 450. In certain embodiments, m is 15. In other embodiments, m is a number from 15 to 20, or from 15 to 25, or from 15 to 50, or from 15 to 100, or from 15 to 150, or from 15 to 200, or from 15 to 250, or from 15 to 300, or from 15 to 350, or from 15 to 400, or from 15 to 450. In certain embodiments, m is 20. In other embodiments, m is a number from 20 to 25, or from 20 to 50, or from 20 to 100, or from 20 to 150, or from 20 to 200, or from 20 to 250, or from 20 to 300, or from 20 to 350, or from 20 to 400, or from 20 to 450.

In certain embodiments, m is 25. In some embodiments, m is a number from 25 to 50. In some embodiments, m is a number from 25 to 100. In some embodiments, m is a number from 25 to 150. In some embodiments, m is a number from 25 to 200. In some embodiments, m is a number from 25 to 250. In some embodiments, m is a number from 25 to 300. In some embodiments, m is a number from 25 to 350. In some embodiments, m is a number from 25 to 400. In some embodiments, m is a number from 25 to 450.

In certain embodiments, m is 50. In some embodiments, m is a number from 50 to 100. In some embodiments, m is a number from 50 to 150. In some embodiments, m is a number from 50 to 200. In some embodiments, m is a number from 50 to 250. In some embodiments, m is a number from 50 to 300. In some embodiments, m is a number from 50 to 350. In some embodiments, m is a number from 10 to 400. In some embodiments, m is a number from 50 to 450.

In certain embodiments, m is 100. In other embodiments, m is a number from 100 to 150, or from 100 to 200, or from 100 to 250, or from 100 to 300, or from 100 to 350, or from 100 to 400, or from 100 to 450. In certain embodiments, m is 150. In other embodiments, m is a number from 150 to 200, or from 150 to 250, or from 150 to 300, or from 150 to 350, or from 150 to 400, or from 150 to 450. In certain embodiments, m is 200. In other embodiments, m is a number from 200 to 250, or from 200 to 300, or from 200 to 350, or from 200 to 400, or from 200 to 450. In certain embodiments, m is 250. In other embodiments, m is a number from 250 to 300, or from 250 to 350, or from 250 to 400, or from 250 to 450. In certain embodiments, m is 300. In other embodiments, m is a number from 300 to 350, or from 300 to 400, or from 300 to 450. In certain embodiments, m is 350. In other embodiments, m is a number from 350 to 400, or from 350 to 450. In certain embodiments, m is 400. In other embodiments, m is a number from 400 to 450.

In some embodiments, m is a number from 100 to 200. In some embodiments, m is a number from 200 to 300. In some embodiments, m is a number from 10 to 400 or more. In some embodiments, m=3x, wherein x is a number from 1 to 100, e.g., x=1 and m=3; x=2 and m=6; x=20 and m=60; x=50 and m=150; x=60 and m=180; etc. The present invention is not limited to the aforementioned values for m.

In some embodiments, the number of pentapeptide repeats (i.e., the aforementioned m variable and the below mentioned n variable) are chosen such that the resulting ELP has a preferred size of about 100 kg/mol. In other embodiments, the preferred size of the ELP is ≤100 kg/mol. In certain embodiments, the maximum size of the ELP is 150-200 kg/mol. In further embodiments, the minimum size of the ELP is 10 kg/mol. In other embodiments, the number of pentapeptide repeats (i.e., the aforementioned m variable) is chosen such that the resulting ELP has a size of about 10 kg/mol to 50 kg/mol, or about 10 kg/mol to 100 kg/mol, or about 10 kg/mol to 125 kg/mol, or about 10 kg/mol to 150 kg/mol, or about 10 kg/mol to 175 kg/mol, or about 10 kg/mol to 200 kg/mol, or about 10 kg/mol to 225 kg/mol, or about 10 kg/mol to 250 kg/mol, or about 100 kg/mol to 125 kg/mol, or about 100 kg/mol to 150 kg/mol, or about 100 kg/mol to 175 kg/mol, or about 100 kg/mol to 200 kg/mol, or about 100 kg/mol to 225 kg/mol, or about 100 kg/mol to 250 kg/mol, or about 125 kg/mol to 150 kg/mol, or about 125 kg/mol to 175 kg/mol, or about 125 kg/mol to 200 kg/mol, or about 125 kg/mol to 225 kg/mol, or about 125 kg/mol to 250 kg/mol, or about 150 kg/mol to 175 kg/mol, or about 150 kg/mol to 200 kg/mol, or about 150 kg/mol to 225 kg/mol, or about 150 kg/mol to 250 kg/mol, or about 175 kg/mol to 200 kg/mol, or about 175 kg/mol to 225 kg/mol, or about 175 kg/mol to 250 kg/mol, or about 200 kg/mol to 225 kg/mol, or about 200 kg/mol to 250 kg/mol, or about 225 kg/mol to 250 kg/mol.

TABLE 2

Shows non-limiting examples of pentapeptide repeats that could be as an ELP in the AMP biopolymer compositions as described herein:

| Pentapeptide Repeat | SEQ ID NO: |
|---|---|
| (VPGYG)$_m$ | 3 |
| (VPGAG)$_m$ | 4 |
| (VPGSG)$_m$ | 5 |
| (VPGGG)$_m$ | 6 |
| (VPGRG)$_m$ | 7 |
| (VPGNG)$_m$ | 8 |
| (VPGDG)$_m$ | 9 |
| (VPGCG)$_m$ | 10 |
| (VPGQG)$_m$ | 11 |
| (VPGEG)$_m$ | 12 |
| (VPGHG)$_m$ | 13 |
| (VPGIG)$_m$ | 14 |
| (VPGLG)$_m$ | 15 |
| (VPGKG)$_m$ | 16 |
| (VPGMG)$_m$ | 17 |
| (VPGFG)$_m$ | 18 |

TABLE 2-continued

Shows non-limiting examples of pentapeptide repeats that could be as an ELP in the AMP biopolymer compositions as described herein:

| Pentapeptide Repeat | SEQ ID NO: |
|---|---|
| (VPGTG)$_m$ | 19 |
| (VPGWG)$_m$ | 20 |
| (VPGVG)$_m$ | 21 |
| (VGGVG)$_m$ | 22 |
| (KGGVG)$_m$ | 23 |
| (VPYGG)$_m$ | 24 |
| (VPYVG)$_m$ | 25 |
| (VPYNG)$_m$ | 26 |
| (VPYCG)$_m$ | 27 |
| (VPYLG)$_m$ | 28 |
| (VPNGG)$_m$ | 29 |
| (IPGYG)$_m$ | 30 |
| (IPGVG)$_m$ | 31 |
| (IPYGG)$_m$ | 32 |
| (IPYVG)$_m$ | 33 |
| (IPYLG)$_m$ | 34 |
| (IPNGG)$_m$ | 35 |
| (LPGYG)$_m$ | 36 |
| (LPGVG)$_m$ | 37 |
| (LPYGG)$_m$ | 38 |
| (LPYVG)$_m$ | 39 |
| (LPYLG)$_m$ | 40 |
| (LPNGG)$_m$ | 41 | where m is from 10 to 400.

In some embodiments, the ELP of the AMP biopolymer compositions as described herein may comprise one or more pentapeptide repeats (see Table 2) consecutively linked. In other embodiments, the one or more pentapeptide repeats may comprise varying m values. For example, an ELP may comprise the sequence ((VPGYG (SEQ ID NO: 3)$_{10}$ (VPGAG (SEQ ID NO: 4)$_{20}$)$_n$, where n is 1 to 14. In some embodiments, the pentapeptide repeats may be arranged in various configurations to create an ELP. For example, ((SEQ ID NO: 1)$_m$ (SEQ ID NO: 3)$_m$ (SEQ ID NO: 1)$_m$)$_n$, or ((SEQ ID NO: 1)$_m$ (SEQ ID NO: 24)$_m$ (SEQ ID NO: 1)$_m$)$_n$, or ((SEQ ID NO: 1)$_m$ (SEQ ID NO: 30)$_m$ (SEQ ID NO: 1)$_m$)$_n$, or ((SEQ ID NO: 1)$_m$ (SEQ ID NO: 33)$_m$ (SEQ ID NO: 1)$_m$)$_n$, or ((SEQ ID NO: 1) (SEQ ID NO: 36)$_m$ (SEQ ID NO: 1)$_m$)$_n$, or ((SEQ ID NO: 1)$_m$ (SEQ ID NO: 39)$_m$ (SEQ ID NO: 1)$_m$)$_n$, or ((SEQ ID NO: 2)$_m$ (SEQ ID NO: 3)$_m$ (SEQ ID NO: 2)$_m$)$_n$, or ((SEQ ID NO: 2)$_m$ (SEQ ID NO: 24)$_m$ (SEQ ID NO: 2)$_m$)$_n$, or ((SEQ ID NO: 2)$_m$ (SEQ ID NO: 30)$_m$ (SEQ ID NO: 2)$_m$)$_n$, or ((SEQ ID NO: 2)$_m$ (SEQ ID NO: 33)$_m$ (SEQ ID NO: 2)$_m$)$_n$, or ((SEQ ID NO: 2)$_m$ (SEQ ID NO: 36)$_m$ (SEQ ID NO: 2)$_m$)$_n$, or ((SEQ ID NO: 2)$_m$ (SEQ ID NO: 39)$_m$ (SEQ ID NO: 2)$_m$)$_n$, or ((SEQ ID NO: 2)$_m$ (SEQ ID NO: 40)$_m$ (SEQ ID NO: 2)$_m$)$_n$, where m is 10-400 and n is 10-400.

In the subsequent examples of ELP formulas shown below, it is noted that the pentapeptide repeats comprising the ELP are shown with varying m values. Therefore for ease of understanding m has been expanded to include j, k, and l. For example, (VPGAG (SEQ ID NO: 4)$_m$ (VPGYG (SEQ ID NO: 3))$_m$ (VPGAG (SEQ ID NO: 4))$_m$ is the same as (VPGAG (SEQ ID NO: 4))$_m$ (VPGYG (SEQ ID NO: 3))$_k$(VPGAG (SEQ ID NO: 4))$_l$ or ELP(A$_j$Y$_k$A$_l$) (as shown below).

In some embodiments, the ELP comprises the formula ELP(X$_j$Y$_k$X$_l$)$_n$, wherein X is SEQ ID NO: 1 (VPGXaaG), and Y is SEQ ID NO: 3 (VPGYG). Thus, the ELP may comprise the formula [(VPGXaaG)$_j$ (VPGYG)$_k$ (VPGXaaG)$_l$]$_n$, e.g., [(SEQ ID NO: 1)$_j$(SEQ ID NO: 3)$_k$ (SEQ ID NO: 1)$_l$]$_n$. For example, in some embodiments, Xaa is alanine and the formula is ELP(A$_j$Y$_k$A$_l$)$_n$, which=[(VPGAG)$_j$(VPGYG)$_k$(VPGAG)$_l$]$_n$ (wherein VPGAG is SEQ ID NO: 4).

In some embodiments, Xaa is serine and the formula is ELP(S$_j$Y$_k$S$_l$)$_n$, which=[(VPGSG)$_j$(VPGYG)$_k$(VPGSG)$_l$]$_n$ (wherein VPGSG is SEQ ID NO: 5). Xaa is not limited to serine or alanine. In some embodiments, Xaa is glycine (and the formula is ELP(G$_j$Y$_k$G$_l$)$_n$). In some embodiments, Xaa is arginine (and the formula is ELP(R$_j$Y$_k$R$_l$)$_n$). In some embodiments, Xaa is asparagine (and the formula is ELP (N$_j$Y$_k$N$_l$)$_n$). In some embodiments, Xaa is aspartic acid (and the formula is ELP(D$_j$ Y$_k$D$_l$)$_n$). In some embodiments, Xaa is cysteine (and the formula is ELP(C$_j$Y$_k$C$_l$)$_n$). In some embodiments, Xaa is glutamine (and the formula is ELP (Q$_j$Y$_k$Q$_l$)$_n$). In some embodiments, Xaa is glutamic acid (and the formula is ELP(E$_j$Y$_k$E$_l$)$_n$). In some embodiments, Xaa is histidine (and the formula is ELP(H$_j$Y$_k$H$_l$)$_n$). In some embodiments, Xaa is isoleucine (and the formula is ELP (I$_j$Y$_k$I$_l$)$_n$). In some embodiments, Xaa is leucine (and the formula is ELP(L$_j$Y$_k$L$_l$)$_n$). In some embodiments, Xaa is lysine (and the formula is ELP(K$_j$Y$_k$K$_l$)$_n$). In some embodiments, Xaa is methionine (and the formula is ELP(M$_j$Y$_k$M$_l$)$_n$). In some embodiments, Xaa is phenylalanine (and the formula is ELP(F$_j$Y$_k$F$_l$)$_n$). In some embodiments, Xaa is threonine (and the formula is ELP(T$_j$Y$_k$T$_l$)$_n$). In some embodiments, Xaa is tryptophan (and the formula is ELP(W$_j$Y$_k$W$_l$)$_n$). In some embodiments, Xaa is tyrosine (and the formula is ELP(Y$_j$Y$_k$Y$_l$)$_n$). In some embodiments, Xaa is valine (and the formula is ELP(V$_j$Y$_k$V$_l$)$_n$).

In some embodiments, ranges for j, k, and l for the pentapeptide repeats depend on the hydrophobicity of the amino acids in the selected pentapeptide repeats. In some embodiments, the variables j, k, and l are equivalent to the m variable and thus may be any number that m is equal to.

For example, in certain embodiments, the variables j, k, or l are 10. In other embodiments, the variables j, k, and l are a number from 10 to 15, or from 10 to 20, or from 10 to 25, or from 10 to 50, or from 10 to 100, or from 10 to 150, or from 10 to 200, or from 10 to 250, or from 10 to 300, or from 10 to 350, or from 10 to 400, or from 10 to 450. In certain embodiments, the variables j, k, or l are 15. In other embodiments, the variables j, k, or l are a number from 15 to 20, or from 15 to 25, or from 15 to 50, or from 15 to 100, or from 15 to 150, or from 15 to 200, or from 15 to 250, or from 15 to 300, or from 15 to 350, or from 15 to 400, or from 15 to 450. In certain embodiments, the variables j, k, or l are 20. In other embodiments, the variables j, k, or l are a number from 20 to 25, or from 20 to 50, or from 20 to 100, or from 20 to 150, or from 20 to 200, or from 20 to 250, or from 20 to 300, or from 20 to 350, or from 20 to 400, or from 20 to 450. In certain embodiments, the variables j, k, or l are 25. In some embodiments, the variables j, k, or l are a number from 25 to 50, or from 25 to 100, or from 25 to 150, or from 25 to 200 or from 25 to 250, or from 25 to 300, or from 25 to 350, or from 25 to 400 or from 25 to 450. In certain embodiments, the variables j, k, or l are 50. In some embodiments, the variables j, k, or l are a number from 50 to 100 or from 50 to 150 or from 50 to 200, or from 50 to 250, or from 50 to 300, or from 50 to 350, or from 10 to 400, or from 50 to 450.

In certain embodiments, the variables j, k, or l are 100. In other embodiments, the variables j, k, or l are a number from 100 to 150, or from 100 to 200, or from 100 to 250, or from 100 to 300, or from 100 to 350, or from 100 to 400, or from 100 to 450. In certain embodiments, the variables j, k, or l are 150. In other embodiments, the variables j, k, or l are a number from 150 to 200, or from 150 to 250, or from 150 to 300, or from 150 to 350, or from 150 to 400, or from 150 to 450. In certain embodiments, the variables j, k, or l are 200. In other embodiments, the variables j, k, or l are a number from 200 to 250, or from 200 to 300, or from 200 to 350, or from 200 to 400, or from 200 to 450. In certain embodiments, the variables j, k, or l are 250. In other embodiments, the variables j, k, or l are a number from 250 to 300, or from 250 to 350, or from 250 to 400, or from 250 to 450. In certain embodiments, the variables j, k, or l are 300. In other embodiments, the variables j, k, or l are a number from 300 to 350, or from 300 to 400, or from 300 to 450. In certain embodiments, the variables j, k, or l are 350. In other embodiments, the variables j, k, or l are a number from 350 to 400, or from 350 to 450. In certain embodiments, the variables j, k, or l are 400. In other embodiments, the variables j, k, or l are a number from 400 to 450.

In further embodiments, j=1, 2, 3, 4, 5, 6, etc. In some embodiments, k=1, 2, 3, 4, 5, 6, etc. In some embodiments, l=1, 2, 3, 4, 5, 6, etc.

In some embodiments, n is greater than 10. In other embodiments, n is less than 400. In certain embodiments, n is 10. In other embodiments, n is a number from 10 to 450, or from 10 to 400, or from 10 to 350, or from 10 to 300, or from 10 to 250, or from 10 to 200, or from 10 to 150, or from 10 to 100, or from 10 to 50. In certain embodiments, n is 50. In other embodiments, n is a number from 50 to 450, or from 50 to 400, or from 50 to 350, or from 50 to 300, or from 50 to 250, or from 50 to 200, or from 50 to 150, or from 50 to 100. In certain embodiments, n is 100. In other embodiments, n is a number from 100 to 450, or from 100 to 400, or from 100 to 350, or from 100 to 300, or from 100 to 250, or from 100 to 200, or from 100 to 150. In certain embodiments, n is 150. In other embodiments, n is a number from 150 to 450, or from 150 to 400, or from 150 to 350, or from 150 to 300, or from 150 to 250, or from 150 to 200. In certain embodiments, n is 200. In other embodiments, n is a number from 200 to 450, or from 200 to 400, or from 200 to 350, or from 200 to 300, or from 200 to 250. In certain embodiments, n is 250. In other embodiments, n is a number from 250 to 450, or from 250 to 400, or from 250 to 350, or from 250 to 300. In certain embodiments, n is 300. In other embodiments, n is a number from 300 to 450, or from 300 to 400, or from 300 to 350. In certain embodiments, n is 350. In other embodiments, n is a number from 350 to 450, or from 350 to 400. In certain embodiments, n is 400. In other embodiments, n is a number from 400 to 450.

In further embodiments, n=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, more than 50 etc.

In some embodiments, the variable for the ELP (e.g., ((pentapeptide repeats) (pentapeptide repeats) (pentapeptide repeats)$_l)_n$, where the variables are j, k, l and n) are selected such that $10 \leq ((j+k+l) \times n) \leq 400$. In some embodiments, the variable for the ELP (e.g., ((pentapeptide repeats) (pentapeptide repeats) (pentapeptide repeats)$_l)_n$, where the variables are j, k, l and n) are selected according to the formula $10 \leq (j+k+l) \times n) \leq 400$.

Without wishing to limit the present invention to any theory or mechanism, n may be determined based on what works well for purification processes, e.g., n may need to be large enough for purification. However, n is not limited to any particular number. In some embodiments, n is 3 or more, 4 or more, 5 or more, etc., e.g., in some embodiments, n=4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, more than 50, etc.

In some embodiments, the n variable (and the aforementioned m variable) is chosen such that the resulting ELP has a preferred size of about 100 kDa to 150 kDa. In some embodiments, the n variable and the aforementioned m variable) is chosen such that the resulting ELP has a size of about 10 kDa to 250 kDa, or about 10 kDa to 200 kDa, or about 10 kDa to 150 kDa, or about 10 kDa to 100 kDa, or about 10 kDa to 50 kDa, or about 10 kDa to 25 kDa, 25 kDa to 250 kDa, or about 25 kDa to 200 kDa, or about 25 kDa to 150 kDa, or about 25 kDa to 100 kDa, or about 25 kDa to 50 kDa, or about 50 kDa to 250 kDa, or about 50 kDa to about 200 kDa, or about 50 kDa to about 150 kDa, or about 50 kDa to about 100 kDa, or about 100 kDa to 250 kDa, or about 100 kDa to about 200 kDa, or about 100 kDa to about 150 kDa, or about 150 kDa to 250 kDa, or about 150 kDa to about 200 kDa, or about 200 kDa to 250 kDa.

In some embodiments, n is from 10 to 400. In other embodiments, n is greater than 10 and less than 400. In further embodiments, the ELP formula comprises $10 \leq (j+k+l) \times n \leq 400$. In some embodiments, the ELP formula comprises $10 \leq (j+k+l) \times n \leq 450$.

In some embodiments, the ELP comprises tyrosine residues (ELP(Tyr)) (VPGYG)$_m$ SEQ ID NO: 3)). In some embodiments, an ELP comprising a pentapeptide repeat comprising a tyrosine residue (Y) allows for it to be photo-crosslinked to ultimately create a hydrogel or biopolymer material.

The $T_t$ of an ELP is adjustable by combining polar and non-polar amino acids in the non-conserved $X_{aa}$ position, and controlling the ELP molar masses. An ELP with Tyr and Ala or Tyr and Ser residues in the $X_{aa}$ position of SEQ ID NO: 1 is shown in Table 3 below. Note that ELP $(A_2Y_1A_2)_{36}$=[(VPGAG)$_2$ (VPGYG)$_1$ (VPGAG)$_2$]$_{36}$ (Xaa is alanine). ELP $(S_2Y_1S_2)_{36}$=[(VPGSG)$_2$ (VPGYG)$_1$ (VPGSG)$_2$]$_{36}$ (Xaa is serine). ELP $(S_2Y_1S_1)_{45}$=[(VPGSG)$_2$ (VPGYG)$_1$ (VPGSG)$_1$]$_{45}$ (Xaa is serine). ELP $(A_2Y_1A_1)_{45}$= [(VPGAG)$_2$ (VPGYG)$_1$ (VPGAG)$_1$]$_{45}$ (Xaa is alanine).

Figure 4:
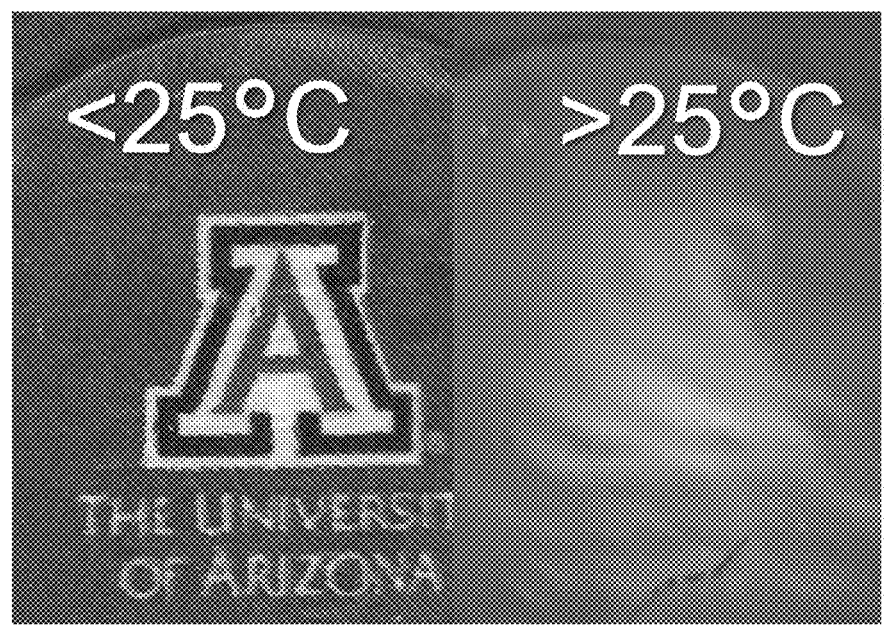
FIG. 4 shows a hydrogel made of cross-linked ELP $(A_2Y_1A_2)_{24}$ showing hydrogel thermoresponsive behavior where the hydrogel is clear below the transition temperature (e.g., below 25° C., left panel) and cloudy above the transition temperature (e.g., above 25° C., right panel).

In some embodiments, an ELP has high conformational flexibility at low temperatures such that it appears clear and has a disordered molten globule aggregate at higher temperatures such that it appears cloudy (see FIG. 4)

TABLE 3

Proposed ELP(Tyr) sequences and their expected and experimental transition temperature ($T_t$)

| ELP (Tyr) | $T_{t,\,expected}$ | Number of ELP pentapeptide (m) | $T_{t,\,experimental}$ of ELP (Tyr) |
|---|---|---|---|
| ELP $(A_2Y_1A_2)_{36}$ | 25° C. | 180 | 25° C. |
| ELP $(S_2Y_1S_2)_{36}$ | 29° C. | 180 | 29° C. (expected) |
| ELP $(S_2Y_1S_1)_{45}$ | 24° C. | 180 | TBD |
| ELP $(A_2Y_1A_1)_{45}$ | 20° C. | 180 | TBD |

Expected $T_t$ ($T_{t,expected}$) and Experimental $T_t$ ($T_{t,experimental}$) are according to previous research by Ingrole, R., Tao et al. "*Synthesis and Immunogenicity Assessment of Elastin-Like Polypeptide-M2e Construct as an Influenza Antigen*" Nano Life, 2014. These results were obtained using alanine in the Xaa position instead of serine, e.g. ELP$(A_2Y_1A_2)$, vs. ELP$(S_2Y_1S_2)_n$. The expected $T_t$ ($T_{t,expected}$) of ELP$(A_2Y_1A_2)_n$ matched the experimental $T_t$ ($T_{t,experimental}$) when the number of ELP pentapeptide repeats were 180 (n=36). The $T_t$ of the ELP can be changed when fused to AMPs but the larger ELP$(A_2Y_1A_2)_{36}$ had less change in $T_t$ when fused to a hydrophilic peptide relative to the smaller ELP$(A_2Y_1A_2)_{24}$.

The ELPs herein were designed based on ELP(Tyr) sequences with the same number of ELP pentapeptide repeats (to similarly match the $T_{t,experimental}$ of ELP(Tyr) with the $T_{t,expected}$ (see Table 3). The sequence variants facilitate: (i) $T_t$ of ELP(Tyr) between room temperature (RT) and body temperature (BT) when fused with amphiphilic AMPs; and (ii) investigation of the relationship between AMP activity and the quantity of Tyr residues, which influences the strength of the film/coating materials. LL37 is a cationic, amphiphilic, antimicrobial peptide, composed of 37 amino acids. The present invention provides a fusion of the LL37 peptide to the C-terminus of ELP(Tyr): ELP(Tyr)-LL37. LL37 can damage microbial membranes, including *E. coli* and *S. aureus*, via carpet or toroidal models. Solid-state NMR spectroscopy revealed that LL37 forms dimer or tetramer oligomer structures like the Barrel-Stave pore model when they bind to the membrane. Since LL37 covers the most-widely accepted microbe lysis mechanisms, it was chosen as a representative model of AMP lysis activity as part of the artificial protein.

Figure 2A:
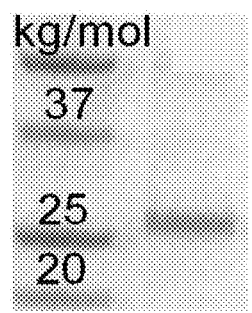
FIG. 2A shows SDS-PAGE analysis of $ELP(A_1Y_1A_1)_{24}$-LL37 purified by inverse transition cycling methods.
Figure 2B:
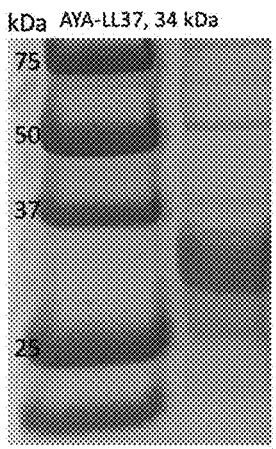
FIG. 2B shows SDS-PAGE analysis of $ELP(S_2Y_1S_2)_8$-LL37 purified by salting out methods.
Figure 2C:
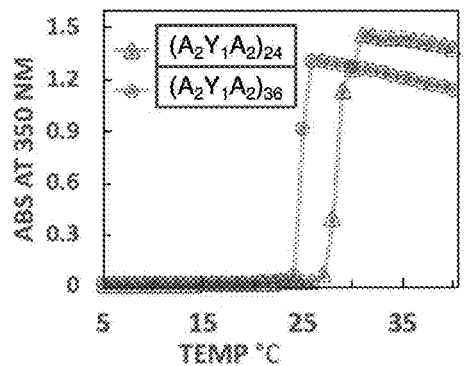
FIG. 2C shows UV/Vis spectrophotometer analysis of the phase-transitioning temperatures of $ELP(A_2Y_1A_2)_{24}$ and $ELP(A_2Y_1A_2)_{36}$, respectively.

The short ELP$(S_2Y_1S_2)_8$-LL37 gene was designed with multiple restriction enzyme sites for gene editing. The gene was cloned into a protein expression vector (see FIG. 1 for a schematic view) and was produced in *E. coli*. The $T_t$ of ELP$(S_2Y_1S_2)_8$-LL37 was too high to apply non-chromatographic $T_t$ purification (>70° C.). Its size was confirmed by metal ion affinity chromatography by attaching the affinity tag to the protein (see FIG. 3). FIG. 2A shows SDS-PAGE analysis of $(S_2Y_1S_2)_8$-LL37 purified by Ni-NTA chromatography methods. FIG. 2B shows SDS-PAGE analysis of ELP$(A_1Y_1A_1)_{24}$-LL37 purified by inverse transition cycling methods. FIG. 2C shows UV/Vis spectrophotometer analysis of the phase-transitioning temperatures of ELP$(A_2Y_1A_2)_{24}$ and ELP$(A_2Y_1A_2)_{36}$, respectively.

Figure 3:
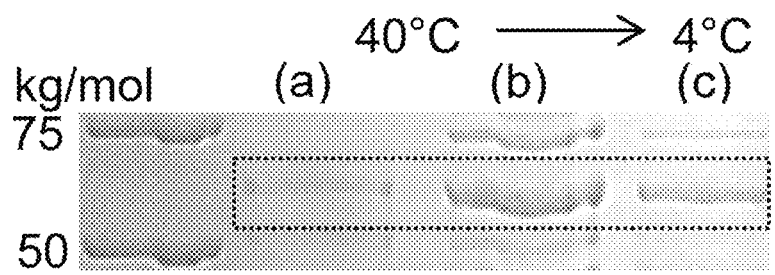
FIG. 3 shows $ELP(S_2Y_2S_2)_{16}$-LL37 with PBS containing 25 wt % ammonium sulfate. At 40° C., the protein was not in solution (a), but the protein was in precipitate (b) and dissolved (c) at 4° C.

The size of the ELP was doubled using the golden gate cloning method, and the phase transition of ELP was captured by decreasing the $T_t$ in a solution with high salt concentration (see FIG. 3). This approach did not work with the shorter ELP, indicating larger ELPs exhibit lower $T_{t,experimental}$ and more closely matched $T_{t,expected}$. Without wishing to limit the present invention to any theory or mechanism, ELP(Tyr)-LL37 proteins may reach the target $T_t$ and facilitate non-chromatographic ELP-fusion protein purification by using the inverse transition cycling (ITC) method that utilizes ELP phase changes above and below its $T_t$ (see FIG. 3).

Inexpensive purification of elastin-like polypeptides (ELP), including ELP(Tyr) and biopolymers containing ELP is carried out through the Inverse Transition Cycling (ITC) method by utilizing the ELP phase change behavior, where ELP phase changes occur at its transition temperature ($T_t$). $T_t$ is determined by the polarity of amino acids in the Xaa position and quantity of pentapeptide repeats in ELP. Below its $T_t$, ELP is soluble and above its $T_t$, ELP is insoluble. The ITC method to purify an ELP mixture is carried out by first centrifuging the ELP mixture at a temperature below $T_t$ when ELP is soluble and discarding the pellet. This removes insoluble impurities when ELP is soluble. Next, the temperature of the ELP mixture is raised above $T_t$ causing ELPs to display increased hydrophobic behavior, aggregate and collapse from solution. The ELP mixture is then centrifuged, and the soluble portion is removed. This removes soluble impurities when ELP is insoluble. Repeating this process several times yields highly pure ELP as many impurities cannot reversibly precipitate and dissolve in solutions.

To capture target proteins, chromatography often requires expensive columns as in ion-exchange or size exclusion, or peptide tags (e.g. His-Tag, Strep-Tag, etc.) on the protein as well as expensive beads (e.g. Ni-NTA beads) used for binding. ITC purification is a less expensive option because it simply requires heating, cooling and centrifugation.

FIG. 4 shows a hydrogel made of cross-linked ELP $(A_2Y_1A_2)_{24}$ showing hydrogel thermoresponsive behavior where the hydrogel is clear below the transition temperature (e.g., below 25° C., left panel) and cloudy above the transition temperature (e.g., above 25° C., right panel).

By genetically fusing AMP to an ELP, *E. coli* host expression, and ITC purification, ELP-AMP can be produced at low cost. $T_t$ behavior of the ELP may depend on environmental factors such as temperature, pH and salt concentrations.

The present invention is not limited to the aforementioned ELPs, e.g., ELP(Tyr). For example, in some embodiments, the ELP comprises ELP(DOPA) after Tyr hydroxylation by tyrosinase.

In some embodiments, the ELP sequence needs to be more hydrophobic than the protein tether. For example, the ratio of hydrophobic to hydrophilic amino acids in ELP needs to be greater than the ratio of hydrophobic to hydrophilic amino acids in the protein tether. In some embodiments, hydrophobic amino acids comprise Valine (Val or V), Isoleucine (Ile or I), Leucine (Leu or L), Methionine (Met or M), Phenylalanine (Phe or F), Tryptophan (Trp or W), Cysteine (Cys or C). In other embodiments, the remaining amino acids (i.e., those not mentioned above) can be considered as hydrophilic or less hydrophobic.

Protein Tethers

As used herein, a "protein tether" or a "peptide tether" may be used interchangeably, and refers to a hydrophilic and unstructured synthetic peptide. In some embodiments, the peptide tether of the antimicrobial composition described herein is more hydrophilic than the ELP sequence. In other embodiments, the ELP sequence of the antimicrobial composition described herein is more hydrophobic than the peptide tether. In further embodiments, the ELP sequence of the antimicrobial composition described herein is more hydrophobic than the peptide tether when counting the number of hydrophobic amino acids in each part (e.g., the ELP sequence has more hydrophobic amino acids than the peptide tether).

One of the unique and inventive technical features of the present invention is utilizing a peptide tether that is more hydrophilic or less hydrophobic than the ELP of the antimicrobial biopolymer composition described herein. Without wishing to limit the invention to any theory or mechanism, it is believed that the technical feature of the present invention advantageously allows for the ELP to form a micelle core and the hydrophilic tether act as a corona in the micelle. This allows the separation of the AMP from the ELP micelle core which improves the AMP activity. If there are no tethers, then some of the ELPs can still form micelle structure but there will be no gap between ELP and AMP. In this design, many AMPs will be buried in the ELP micelle core and thus, the amounts of active AMPs, outside of the micelle cores, will be less than the ELP-tether-AMP design and thus, the relative activity will be dropped.

In some embodiments, the peptide tether comprises the sequence (VSGSG (SEQ ID NO: 42))$_i$, where i is 10 to 400. In other embodiments, the peptide tether comprises the sequence (AGAGAGPEG (SEQ ID NO: 43))$_i$, where i is 1 to 200. In some embodiments, the peptide tether comprises the sequence (VPGAG (SEQ ID NO: 44))$_i$, where i is 10 to 400. In some embodiments, the peptide tether comprises the sequence (VPGGG (SEQ ID NO: 45))$_i$, where i is 10 to 400. In some embodiments, the peptide tether comprises the sequence (VPGEG (SEQ ID NO: 46))$_i$, where i is 10 to 400. In some embodiments, the peptide tether comprises the sequence (VPGEGVPGKG (SEQ ID NO: 47))$_i$, where i is 1 to 200. In some embodiments, the peptide tether comprises the sequence (AGAGAGPEG (SEQ ID NO: 43))$_i$, where i is less than 200. In some embodiments, the peptide tether comprises a sequence (ASPAAPAPASPAAPAPSAPAA (SEQ ID NO: 48))$_i$, where i is 1 to 100. In some embodiments, the peptide tether comprises the sequence (GEQGKPGNQGEPGNPGSPGQPGNPGQPGS PGNPGQPGNEGPQGSQGNPGQPGEPG-SNGQPGQPGQNGKNGQPGSPGSQGSPGNQGSPG-NQGQP GNKGEQGKPGNQGPA (SEQ ID NO: 49))$_i$, where i is is 1 to 20.

In some embodiments, the length or size of the peptide tether (i.e., the i value) is selected to keep the antimicrobial biopolymer composition less than or equal to 100 kDa. In other embodiments, the length or size of the peptide tether (i.e., the i value) is selected to keep the antimicrobial biopolymer composition about 50 kDa. In some embodiments, the length or size of the peptide tether (i.e., the i value) is selected to keep the antimicrobial biopolymer composition about 150 kDa. In other embodiments, the length or size of the peptide tether (i.e., the i value) is selected to keep the antimicrobial biopolymer composition about 100 kDa. In further embodiments, the length or size of the peptide tether (i.e., the i value) is selected to keep the antimicrobial biopolymer composition within about 200 kDa.

In certain embodiments, i is 5. In other embodiments, i is a number from 5 to 10, or from 5 to 20, or from 5 to 25, or from 5 to 50, or from 5 to 100, or from 5 to 150, or from 5 to 200, or from 5 to 250, or from 5 to 300, or from 5 to 350, or from 5 to 400, or from 5 to 450. In certain embodiments, i is 10. In other embodiments, i is a number from 10 to 20, or from 10 to 25, or from 10 to 50, or from 10 to 100, or from 10 to 150, or from 10 to 200, or from 10 to 250, or from 10 to 300, or from 10 to 350, or from 10 to 400, or from 10 to 450. In certain embodiments, i is 20. In other embodiments, i is a number from 20 to 25, or from 20 to 50, or from 20 to 100, or from 20 to 150, or from 20 to 200, or from 20 to 250, or from 20 to 300, or from 20 to 350, or from 20 to 400, or from 20 to 450. In certain embodiments, i is 50. In other embodiments, i is a number from 50 to 100, or from 50 to 150, or from 50 to 200, or from 50 to 250, or from 50 to 300, or from 50 to 350, or from 50 to 400, or from 50 to 450.

In certain embodiments, i is 100. In other embodiments, i is a number from 100 to 150, or from 100 to 200, or from 100 to 250, or from 100 to 300, or from 100 to 350, or from 100 to 400, or from 100 to 450. In certain embodiments, i is 150. In other embodiments, i is a number from 150 to 200, or from 150 to 250, or from 150 to 300, or from 150 to 350, or from 150 to 400, or from 150 to 450. In certain embodiments, i is 200. In other embodiments, i is a number from 200 to 250, or from 200 to 300, or from 200 to 350, or from 200 to 400, or from 200 to 450. In certain embodiments, i is 250. In other embodiments, i is a number from 250 to 300, or from 250 to 350, or from 250 to 400, or from 250 to 450. In certain embodiments, i is 300. In other embodiments, i is a number from 300 to 350, or from 300 to 400, or from 300 to 450. In certain embodiments, i is 350. In other embodiments, i is a number from 350 to 400, or from 350 to 450. In certain embodiments, i is 400. In other embodiments, i is a number from 400 to 450.

The protein tether separates the ELP and the AMP to increase AMP activity. The protein tether is designed based on currently used synthetic polymer tethers, e.g., polyethylene glycol (PEG), with similar properties: size controlled, hydrophilic, and unstructured. The benefit of designing a protein tether is that the tether can be genetically encoded with ELP and AMP, e.g., ELP-tether-AMP is synthesized together in one polymer unit via bio-manufacturing, and purified (e.g., by ITC), which the conventional approach needs to prepare biomaterials and synthesize and purify polymer tethers and AMPs separately, and then attached end-to-end, resulting in high cost and time.

Without wishing to limit the present invention to any theory or mechanism it is believed that the hydrophilic properties of a synthetic polymer tethers improve AMP stability because the hydration characteristic repels the adherence of nonspecific biomolecules (e.g., proteases), thus preventing peptide (i.e., AMP) degradation. In some embodiments, AMP activity (i.e., antimicrobial activity) may be extended (e.g., extended from hours to days) in vivo when attached to hydrophilic unstructured proteins and indicates that unstructured protein tethers with hydrophilic properties prevent AMP degradation and enhance the stability and activity.

Without wishing to limit the present invention to any theory or mechanism it is believed that the use of a hydrophilic peptide tether helps to improve the stability of the entire antimicrobial composition described herein and enhances antimicrobial activity. Surprisingly, the present invention was able to make use of a hydrophilic peptide tether rather than a synthetic polymer tether to create the biopolymer. The use of a peptide tether is novel in the formation of AMP-biopolymers, because prior art teaches the use of synthetic tether polymers. Additionally, the use of a hydrophilic peptide tether allows the preparation of a cost-effective antimicrobial biopolymer material (i.e., antimicrobial biopolymer composition).

In some embodiments, the hydrophilic tether described herein allows for the AMP and ELP to remain associated together. In other embodiments, the hydrophilic tether described herein allows for the AMP and ELP to remain associated together through the synthesis and purification of the antimicrobial biopolymer composition. Without wishing to limit the present invention to any theory or mechanism it is believed that the ability to to allow the entire antimicrobial biopolymer composition described herein (i.e., the ELP, the AMP, and the peptide tether) to remain associated together through the synthesis and purification of the antimicrobial biopolymer composition allows for a cost effective method of producing the composition described herein because there is no need to methods to attach the three pieces.

Intrinsically disordered proteins have similar flexibility to PEG due to a similar chain stiffness with a persistent length of ~0.4 nm. Hydrophilic unstructured proteins are available with precisely controllable lengths, allowing the development of the protein tether.

The tether is to be hydrophilic, unstructured, and of a certain length. For example, in certain embodiments, the tether length is at least 3000 g/mol, which is equal to a degree of polymerization (DP) of 70. In certain embodiments, for better separation between the self-assembled ELP nanoparticle and AMP, the ratio of tether size to whole biopolymer size ($f_{tether}$)=(molar mass of tether)/(molar mass of ELP-tether-AMP) is about 0.2 as described by Widder et al. in their article "*Characterization of hydration and nanophase separation during the temperature response in hydrophobic/hydrophilic elastin-like polypeptide (ELP) diblock copolymers*", published in the Soft Matter in 2017 (see Table 4).

In some embodiments, the $f_{tether}$ is greater than or equal to 0.2. In other embodiments, the $f_{tether}$ is less than or equal to 0.5. In further embodiments, the $f_{tether}$ is about 0.10, or about 0.15, or about 0.20, or about 0.25, or about 0.30, or about 0.35, or about 0.40, or about 0.45, or about 0.50, or about 0.55, or about 0.60. In some embodiments, the $f_{tether}$ ranges from 0.10 to 0.60, or from 0.10 to 0.50, or from 0.10 to 0.40, or from 0.10 to 0.30, or from 0.10 to 0.20, or from 0.20 to 0.60, or from 0.20 to 0.50, or from 0.20 to 0.40, or from 0.20 to 0.30, or from 0.30 to 0.60, or from 0.30 to 0.50, or from 0.30 to 0.40, or from about 0.40 to 0.60, or from about 0.40 to about 0.50, or about 0.50 to about 0.60.

Without wishing the limit the present invention to any theory or mechanism it is believed that an antimicrobial biopolymer composition (e.g., ELP-tether-AMP) wherein the ratio of tether molar mass (or molecular weight) to total ELP-tether AMP (i.e, $f_{tether}$) is from 0.2 and 0.5, the hydrophobic ELP will form micelle core while hydrophilic or less hydrophobic tether will segregate AMP from the ELP core, meaning that the tether will be the corona of the micelle. In other words, from center to the outside of the micelle will be ELP, tether and AMP, sequentially.

Referring to Table 4 two protein tethers (DP>70 and $f_{tether}$: ~0.2) were introduced into the ELPs: (i) hydrophilic polymer-like unstructured protein $C_{30}$; and (ii) $ELP(S)_m$-$ELP(S)_i$=VPGSG (SEQ ID NO: 5)$_m$; $C_i$=[AGAGAGPEG]$_i$ (SEQ ID NO: 43). Note m is not limited to 36 and 45, and i is not limited to 30 per Table 4.

TABLE 4

Shows non-limiting examples of ELP(Tyr)-protein tether design with LL37

| ELP (Tyr)-tether (ELP(S)$_m$ or C$_i$) | $T_{t, expected}$[37] | m | $F_{tether}$ (Molar mass of tether/molar mass of ELP(Tyr)-tether) | $T_{t, experimental}$ | $T_{t, experimental}$ with LL37 |
|---|---|---|---|---|---|
| ELP(S$_2$Y$_1$S$_2$)$_{36}$-ELP(S)$_{36}$ | 29° C. | 180 | 0.19 | 29° C. (expected) | TBD |
| ELP(A$_2$Y$_1$A$_2$)$_{36}$-ELP(S)$_{36}$ | 26° C. | 180 | 0.20 | 26° C. (expected) | TBD |
| ELP(S$_2$Y$_1$S$_1$)$_{45}$-ELP(S)$_{45}$ | 24° C. | 180 | 0.19 | TBD | TBD |
| ELP(A$_2$Y$_1$A$_1$)$_{45}$-ELP(S)$_{45}$ | 21° C. | 180 | 0.19 | TBD | TBD |
| ELP(S$_2$Y$_1$S$_2$)$_{36}$-C$_{30}$ | >29° C. | 180 (tether not included) | 0.21 | TBD | TBD |
| ELP(A$_2$Y$_1$A$_2$)$_{36}$-C$_{30}$ | >25° C. | 180 (tether not included) | 0.22 | TBD | TBD |
| ELP(S$_2$Y$_1$S$_1$)$_{45}$-C$_{30}$ | >25° C. | 180 (tether not included) | 0.21 | TBD | TBD |
| ELP(A$_2$Y$_1$A$_1$)$_{45}$-C$_{30}$ | >20° C. | 180 (tether not included) | 0.22 | TBD | TBD |

To test hydration characteristics of hydrophilic protein tethers, the hydrodynamic radius ($r_h$) of nanoparticles can be measured to observe changes of particle sizes compared to ELP(S$_2$Y$_1$S$_2$)$_{36}$ (Table 3) vs. ELP(S$_2$Y$_1$S$_1$)$_{36}$-ELP(S)$_{36}$ (Table 4), which have the same amino acid compositions but different distributions; in the absence and presence of protein tethers, the contact angle of water droplets on the AMP biopolymer films and coatings on silica can be analyzed (Table 3 and Table 4); and (iii) anti-adhesion or anti-fouling functionality will be identified via fluorescent microscopy using fluorescent-tagged bovine serum albumin on the AMP biopolymer coatings, and the result can be compared to PEG coatings. Since hydrophilic synthetic polymer PEG is a well-known conventional tether with excellent antifouling property, the last test will help to select a protein tether in Table 4 that shows promising results.

To examine plasma or serum stability of LL37 in the compositions of the present invention, samples of LL37 and ELP(Tyr)-tether-LL37 nanoparticles will be collected in 80% human plasma or serum at 37° C. in time intervals. Biomolecules in the serum will be heat-inactivated right after the sample collection to prevent additional LL37 degradation, and the percentage of degradation will be analyzed by HPLC.

Antimicrobial Peptides (AMPs)

As used herein, "antimicrobial peptides (AMPs)" refers to a class of small, positively charged peptides that widely exist in nature and they are an important part of the innate immune system of different organisms. AMPs are evolutionarily conserved and have a broad range of antimicrobial activity inhibitory effects against bacteria, fungi, parasites, and viruses. Additionally, AMPs are relatively short, commonly comprising 10-60 amino acids, contain a substantial proportion (typically 50%) of hydrophobic residues, and are often cationic or zwitterionic. In some embodiments, AMPs may be classified into four categories based on their secondary structure, i.e., (i) α-helical, (ii) β-sheet, (iii) αβ, or (iv) non-αβ elements.

Without wishing to limit the present invention to any theories or mechanisms it is believed that because AMPs are generally small peptides (e.g., 10-60aa) with a simple structure, AMPs are able to maintain their activities over time because they are less likely to lose their structure and therefore their function.

In some embodiment, the antimicrobial peptide (AMP) selected for the antimicrobial compositions described herein may be selected based on the resulting material (e.g., micelle or nanoparticles, hydrogel, films or adhesives) in which the antimicrobial composition will be utilized in. For example, in some embodiments, to create a hydrogel, a film or an adhesive material using the antimicrobial composition described herein, tyrosine residues of the ELP need to be photocrosslinked or hydrolyzed and thus, AMPs without tyrosine residues should be used. Otherwise, AMPs will be also crosslinked or hydrolyzed and thus cannot be used as AMPs. In other embodiments, to create a micelle or nanoparticle material using the antimicrobial composition described herein AMPs with tyrosine residues may still be used. In some embodiments, to create a micelle or nanoparticle material the total amount of hydrophobic amino acid residues in the AMP needs to be less than the ELP. Without wishing to limit the present invention to any theory or mechanisms it is believed that an antimicrobial composition (such as the one described herein) with an ELP that is more hydrophobic than the AMP, can form a micelle core at a certain threshold temperature and peptide tether will segregate AMPs away from the ELP micelle core.

In some embodiments, the antimicrobial compositions described herein comprise an antimicrobial peptide (AMP). In other embodiments, the antimicrobial compositions described herein comprise an antimicrobial peptide (AMP) with no tyrosine amino acids. In some embodiments, the AMP comprises no tyrosine amino acid residues within its sequence. In other embodiments, the AMP sequence comprises no tyrosine amino acid residues. In some embodiments, the antimicrobial peptide (AMP) can be any AMP with no tyrosine amino acid residue.

The antimicrobial peptide (AMP) may be selected from one of many known AMPs or those in future development. The present invention is not limited to the AMPs disclosed herein. A non-limiting example of an AMP is LL37, which is a cationic, amphiphilic, antimicrobial peptide, composed of 37 amino acids (LLGDFFRKSKEKIGKEFKRIVQRIKDFLRNLVPRTES, SEQ ID NO: 50).

In some embodiments, the antimicrobial peptides (AMPs) of the compositions as described herein may comprise antibacterial, antifungal, anti-parasitic, antiviral activity (i.e., properties) or a combination thereof. In some embodiments, any antimicrobial peptide (AMP) may be utilized in the composition of the present invention as described herein. In other embodiments, any synthetic or native AMP may be utilized in the composition of the present invention as described herein. Non-limiting examples of AMPs are described in Wang et al., in the article "*APD3: the antimicrobial peptide database as a tool for research and education*," published in Nucleic Acid Research in 2016.

Non-limiting examples of AMPs with antibacterial activity include be are not limited to LL37, RL37, dermcidin, protegrin 1, protegrin 2, protegrin 3, protegrin 4, protegrin 5, abaecin, andropin, bactenecin, bovine neutrophil beta-defensin 12 (bBD-1), Pexiganan, Lytixar, hLF1-11, LL-37, Omiganan, Corticostatin I, Corticostatin VI, NP-3a, Pediocin PA-1/AcH, Lacticin 3147, As-CATH5, Dalbavancin, Baciim, Vancocin, Daptomycin, Colistin, Telavancin, Gramicidin, D2A21, PXL01, Omiganan, Nisin, Polylysine, NKL-24, Caerin1.1, Caerin 1.9, Dicentracin, Thanatin, Ponericin W1, Mastoparan, or a combination thereof.

Non-limiting examples of AMPs with antifungal activity include but are not limited to Lactoferricin B (LfcinB), bombinin-like peptide 1, bombinin-like peptide 3, bombinin-like peptide 7, Antifungal protein (AFP), hLF1-11, Novexatin, CZEN-002, PAC-113, NP-3a, As-CATH5, PAC-113, P-113, D2A21, Omiganan, Polylysine, PAF26, 03TR/C1203TR, Thanatin, Ponericin W1, or a combination thereof.

Non-limiting examples of AMPs with antiparasitic activity include but are not limited to gaegurin-1, gaegurin-2, gaegurin-3, DefMT7 (defensin MT7), or a combination thereof.

Non-limiting examples of AMPs with antiviral activity include but are not limited to antiviral protein Y3, human neutrophil peptide-4 (HNP-4), human defensin 5 (HD-5), human defensin 6 (HD-6), NP-3a, Polylysine, or a combination thereof.

Non-limiting examples of AMPs with anti-cancer activity include but are not limited to Iseganan or Mastoparan. Non-limiting examples of AMPs with anti spermicidal activity include but are not limited to Pediocin PA-1/AcH, or Lacticin 3147. Non-limiting examples of AMPs with anti-sepsis activity include but are not limited to As-CATH5. Non-limiting examples of AMPs with anti-HIV-1 activity include but are not limited to Fuzeon.

Non-limiting examples of AMPs include but are not limited to LL37, RL37, dermcidin, protegrin 1, protegrin 2, protegrin 3, protegrin 4, protegrin 5, abaecin, andropin, bactenecin, bovine neutrophil beta-defensin 12 (bBD-1), Pexiganan, Lytixar, hLF1-11, LL-37, Omiganan, Corticostatin I, Corticostatin VI, NP-3a, Pediocin PA-1/AcH, Lacticin 3147, As-CATH5, Dalbavancin, Baciim, Vancocin, Daptomycin, Colistin, Telavancin, Gramicidin, D2A21, PXL01, Omiganan, Nisin, Polylysine, NKL-24, Caerin1.1, Caerin 1.9, Dicentracin, Thanatin, Ponericin W1, Mastoparan, Lactoferricin B (LfcinB), bombinin-like peptide 1, bombinin-like peptide 3, bombinin-like peptide 7, Antifungal protein (AFP), hLF1-11, Novexatin, CZEN-002, PAC-113, NP-3a, As-CATH5, PAC-113, P-113, D2A21, Omiganan, Polylysine, PAF26, 03TR/C1203TR, Thanatin, Ponericin W1, gaegurin-1, gaegurin-2, gaegurin-3, DefMT7 (defensin MT7), antiviral protein Y3, human neutrophil peptide-4 (HNP-4), human defensin 5 (HD-5), human defensin 6 (HD-6), NP-3a, Polylysine, Iseganan, Mastoparan, Pediocin PA-1/AcH, Lacticin 3147, As-CATH5, Fuzeon, or a combination thereof. However, the present invention is not limited to the aforementioned AMPs.

Regarding orientation of the AMP, AMPs tethered by their N- or C-termini may be more potent than an AMP randomly attached to tethers between its ends. In some embodiments, the AMP is attached to the protein tether at the N-terminal of the AMP. In other embodiments, the AMP is attached to the protein tether at the C-terminal of the AMP.

Without wishing to limit the present invention to any theory or mechanism it is believed that there are three mechanisms that are most-widely accepted for microbe lysis by AMPs (e.g., carpet model, barrel-stave model and toroidal model). First, in the carpet model, AMPs (e.g., cationic AMPs) bind to the membrane surface of the microbe via electrostatic interactions and cover the membrane in a carpet-like manner. Once a critical concentration of AMPs is reached, the AMPs insert into the membrane and distort it; leading to micellization. In the barrel-stave model, AMPs interact laterally with one another and interact with the membrane (e.g., the hydrophobic part of the AMPs interact with the membrane) resulting in the formation of a transmembrane pore with the hydrophilic part of the AMPs facing the inner channel. In the third model, the toroidal pore model, specific AMP-AMP interactions are not present. Instead, AMPs affect the local curvature of the bilayer in a cooperative manner such that a toroid of high curvature forms. The membrane is caused to curve inward, resulting in the formation of a pore made up of AMPs and lipid head groups.

Without wishing to limit the present invention to any theory or mechanism it is believed that AMPs can form barrel-stave pores on microbe membranes, however, for antimicrobial activity, several AMPs in an antiparallel formation are required to form the pore. For example, several LL37 peptides form a barrel structure in an antiparallel orientation and follow the carpet or toroidal model to lyse the bacterial membrane. This covers the three most widely accepted microbe lysis mechanisms. In some embodiments, AMPs described herein for use in the antimicrobial composition described herein may utilize any of the three lysis mechanisms for killing microbes (e.g., bacteria, viruses, fugi, parasites).

The present invention features simple gene editing to encode the AMPs to be connected to a protein tether by either the N- or C-terminus for the same AMP orientation (ELP-tether-AMP or AMP-tether-ELP) within the material. For AMP orientation with opposite direction in the same material, either two AMP molecules can be attached, one by the N- and one by the C-terminus (e.g., AMP-tether-ELP-tether-AMP), or by mixing two proteins (ELP-tether-LL37 and LL37-tether-ELP) in the same biomaterial, the orientation of LL37 can be alternated in the ELP-based nanoparticle, films, and adhesives.

Development of ELP(Tyr)-Tether-AMP Nanoparticle, Film, and Coating Materials

The designed $T_t$ of ELP(Tyr)-AMP facilitates ELP self-assembled nanoparticles at body temperature (BT), while Tyr residues in ELP(Tyr) can be photo-cross-linked to construct ELP(Tyr)-AMP films and hydroxylated to form ELP(DOPA)-AMP adhesives for coating biomaterial surfaces. In some embodiments, L-3,4-dihydroxyphenylalanine (DOPA) is a precursor to dopamine.

For example, because Tyr residues are rare in AMPs, Tyr-crosslinking using ELP(Tyr) helps to mitigate random cross-linking of AMPs and maximize AMP activity.

ELP(DOPA) may be produced by hydroxylating Tyr residues in ELP(Tyr) with commercially available mushroom tyrosinase. The ELP(DOPA)-AMP solution may be dip coated to deposit the ELP(DOPA)-AMP on biomaterial surfaces, such as alumina, Ti alloy, and polymers (e.g., ePTFE). The dwelling time of ELP(DOPA)-AMP adhesives will be monitored on surfaces in physiological buffers at BT, and the concentration of detached ELP(DOPA)-AMP proteins in solution can be determined over time using UV absorbance (280 nm) and the Beer-Lambert law.

An automated antibacterial susceptibility testing instrument can measure the minimal inhibitory concentration of free LL37 and ELP-LL37 nanoparticles against *E. coli* and *S. aureus*. The agar disk-diffusion method can be adapted to test the activity of ELP(Tyr)-LL37 nanoparticles, films and coatings on biomaterial surfaces. For example, MacConkey agar can be prepared for *E. coli* and tryptic soy agar can be prepared for *S. aureus* to determine the LL37 activity level by measuring the zone inhibition around the film or coating material, where >1 mm is indicative of a good antibacterial agent based on Swiss Norm 195920-ASTM E 2149-01.

As previously discussed, the ELP(Tyr)-AMP films herein, using Tyr which is not found in most AMPs for cross-linking, may enhance AMP activity relative to the previously developed ELP-AMP film because AMPs were unintentionally cross-linked, resulting in a decrease in AMP activity.

One of the unique and inventive technical features of the present invention is utilizing specific amino acid residues (i.e, tyrosine (Y)) to crosslink the ELPs and selecting AMPs with no tyrosine (Y) amino acid residues to create an antimicrobial biopolymer composition described herein. Without wishing to limit the invention to any theory or mechanism, it is believed that the technical feature of the present invention advantageously provides for a method to specifically cross-link only the ELP part of the antimicrobial biopolymer composition while other parts of the composition (i.e., the peptide tether and AMPs) will not be cross-linked and thus, the activity (i.e., the antimicrobial activity) of the AMPs will not be hindered.

By cross-linking specific amino acid residues (i.e, tyrosine (Y)) in the platform (i.e., in the ELP) for AMPs, biopolymer networks can be prepared in aqueous conditions (e.g., a hydrogel). The platform design of the present invention reduces unintentional cross-linking of the peptide tether and AMPs. For example, the ELPs are photo-crosslinked using "Y" residues. Selected AMPs for the antimicrobial biopolymer composition described herein do not include "Y" residues and thus, the present invention can specifically cross-link only ELP parts while other parts (i.e., the peptide tether and AMPs) will not be cross-linked, and thus, cross-linking will not hinder AMP activity. All AMP constituents in the ELP-tether-AMP design are expected to be active in the cross-linked or hydrogel materials Furthermore, the prior references teach away from the present invention. For example, in previous designs, platforms were crosslinking by using certain amino acid side chains. However, with this method of crosslinking it is difficult to avoid crosslinking of AMPs. This causes unintentional crosslinking of AMPs and will inhibit the activity of AMPs.

In some embodiments, the antimicrobial biopolymer compositions described herein (e.g., ELP-tether-AMP) will be genetically encoded together on the same plasmid using DNA cloning technology. Then, this ELP-tether-AMP sequence will be expressed using a biosystem (e.g., *E. coli*.) Therefore, "all-in-one" ELP-tether-AMP (i.e., "all-in-one" antimicrobial biopolymer composition) will be synthesized together without additional methods to attach them. In some embodiments, the antimicrobial biopolymer composition of the present invention is an "all-in-one" composition and utilizes various DNA and protein engineering technologies.

Without wishing to limit the present invention to any theories or mechanisms, it is believed that the antimicrobial biopolymer composition of the present invention is cost effective than previous designs because the three components (i.e., the ELP, the AMP, and the peptide tether) are continuously linked throughout the synthesis and purification steps.

Applications

As previously discussed, the biopolymer-AMP compositions (e.g., AMP-ELP platform) have a variety of applications that include but are not limited to: antimicrobial nanoparticles as AMR therapeutics or as a pharmaceutical to treat infected individuals, antimicrobial coatings on clothing, on surfaces of implants, or on medical devices, such as endoscopes, to prevent secondary microorganism infection from the device to patient, antimicrobial filters to prevent transmission and directly kill a broad range of biological pathogens, antimicrobial films for wound dressings, etc.

Without wishing to limit the present invention to any theory or mechanism, it is believed that large-scale production and storage of AMP-ELPs may be a versatile defensive strategy against of a biological warfare agents (BWAs; e.g., *Bacillus anthracis* and *Yersenia pestis*) attack or epidemic since the material can be used directly in applications ranging from a surface coating to protect personnel and infrastructure to a nanoparticle to treat BWA exposure. AMPs have shown efficacy against an extensive range of weaponizable biological pathogens such that having it on hand is invaluable preparation for an unknown or new BWA.

The present invention also provides methods for treating infections. The methods may feature the introduction of a biopolymer-AMP composition of the present invention, wherein the biopolymer-AMP composition kills the infectious agent or reduces the growth of the infectious agent.

The present invention also provides cocktails, e.g., for therapeutic purposes, wherein the cocktails comprise two or more AMP-ELPs such as ELPs with different AMPs, different ELPs with different AMPs, etc.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An antimicrobial biopolymer composition comprising,
   a) an elastin-like polypeptide (ELP), wherein the ELP comprises one or more pentapeptide repeats consecutively linked, wherein at least one of the pentapeptide repeats comprises a tyrosine residue; wherein the one or more pentapeptide repeats are according to the formula (WaaPXaaYaaG (SEQ ID NO: 2))m, where Waa is valine, isoleucine or leucine, where Xaa is any amino acid, where Yaa is any amino acid except for proline, and where m is 10 to 400;
   b) an antimicrobial peptide (AMP); and
   c) a hydrophilic, unstructured peptide tether connecting the ELP and the AMP;

wherein the peptide tether connects to the AMP at the AMP's N-terminus, C-terminus, or both;

wherein the ELP is more hydrophobic than the peptide tether.

2. The composition of claim 1, wherein the one or more pentapeptide repeats is selected from a group consisting of: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

3. The composition of claim 1, wherein the one or more pentapeptide repeats comprising the tyrosine is selected from a group consisting of SEQ ID NO: 3, SEQ ID NO: 24, SEQ ID NO: 25, SEQ ID NO: 26, SEQ ID NO: 27, SEQ ID NO: 28, SEQ ID NO: 30, SEQ ID NO: 32, SEQ ID NO: 33, SEQ ID NO: 34, SEQ ID NO: 36, SEQ ID NO: 38, SEQ ID NO: 39, and SEQ ID NO: 40.

4. The composition of claim 1, wherein the tyrosine residues are cross-linked to form a self-standing film or membrane material.

5. The composition of claim 1, wherein the tyrosine residue allows the composition to adhere to a surface after hydroxylation by tyrosinase.

6. The composition of claim 5, wherein the surface is a cloth, a plastic, a glass, a metal, or a combination thereof.

7. The composition of claim 5, wherein the surface is a medical device, a dressing, a clothing, or a combination thereof.

8. The composition of claim 1, wherein the ELP is according to the formula [(VPGXaaG (SEQ ID NO: 1))$_j$ (VPGYG (SEQ ID NO: 3))$_k$ (VPGXaaG (SEQ ID NO: 1))$_l$]$_n$, where j ranges from 10-400, k ranges from 10-400, l ranges from 10-400, and n ranges from 10-400, such that $10 \le (j+k+l)*n \le 400$.

9. The composition of claim 8, wherein one Xaa of the formula is identical to or different from another Xaa of the formula.

10. The composition of claim 8, wherein Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, or valine.

11. The composition of claim 8, wherein tyrosine residues are cross-linked to form a self-standing film, a membrane material, or a hydrogel.

12. The composition of claim 8, wherein the tyrosine residues allow the composition to adhere to a surface after hydroxylation.

13. The composition of claim 12, wherein the surface is a cloth, a plastic, a glass, a metal, or a combination thereof.

14. The composition of claim 12, wherein the surface is a medical device, a dressing, a clothing, or a combination thereof.

15. The composition of claim 1, wherein the AMP comprises antibacterial activity, antiviral activity, antifungal activity, antiparasitic activity or a combination thereof.

16. The composition of claim 15, wherein the antibacterial AMP comprises LL37, RL37, dermcidin, protegrin 1, protegrin 2, protegrin 3, protegrin 4, protegrin 5, abaecin, andropin, bactenecin, bovine neutrophil beta-defensin 12 (bBD-1), Pexiganan, hLF1-11, LL-37, Corticostatin I, Corticostatin VI, NP-3a, Pediocin PA-1/AcH, Lacticin 3147, As-CATH5, Dalbavancin, Baciim, Daptomycin, Colistin, Telavancin, Gramicidin, D2A$_{21}$, PXL01, Omiganan, Nisin, Polylysine, NKL-24, Caerin1.1, Caerin 1.9, Dicentracin, Thanatin, Ponericin W1, Mastoparan or a combination thereof.

17. The composition of claim 1, wherein the hydrophilic peptide tether comprises [VPGSG]$_i$ (SEQ ID NO: 42) or [AGAGAGPEG]$_m$ (SEQ ID NO: 43), wherein i is equal to 36 or 45 and m is equal to 30.

18. The composition of claim 1, wherein the composition self-assembles into nanoparticles.

19. The composition of claim 1, wherein the hydrophilic peptide tether has anti-fouling characteristics.

* * * * *